United States Patent [19]

Driver

[11] Patent Number: 5,625,459
[45] Date of Patent: Apr. 29, 1997

[54] DIFFUSE REFLECTANCE PROBE

[75] Inventor: Richard D. Driver, Cambridge, Mass.

[73] Assignee: Galileo Electro-Optics Corporation, Sturbridge, Mass.

[21] Appl. No.: 398,595

[22] Filed: Mar. 3, 1995

[51] Int. Cl.$^6$ .............. G01N 21/47; G02B 6/00; G02B 6/26
[52] U.S. Cl. .............. 356/446; 750/559.16; 750/227.24; 385/12; 385/31; 385/33; 385/36; 385/42
[58] Field of Search .............. 356/446; 250/559.16, 250/559.18, 227.24, 227.28, 227.29, 227.32; 385/12, 89, 901, 902, 33, 42, 49, 57, 31, 36, 43

[56] References Cited

U.S. PATENT DOCUMENTS

| | | | |
|---|---|---|---|
| 3,986,778 | 10/1976 | Mathisen et al. | 356/244 |
| 4,022,534 | 5/1977 | Kishner | 356/446 |
| 4,272,156 | 6/1981 | Ishibashi et al. | 385/117 |
| 4,518,259 | 5/1985 | Ward | 356/446 |
| 4,573,761 | 3/1986 | McLachlan et al. | 356/301 |
| 4,610,513 | 9/1986 | Nishioka et al. | 385/117 |
| 4,636,082 | 1/1987 | Barry | 356/446 |
| 4,707,134 | 11/1987 | McLachlan et al. | 356/342 |
| 4,816,670 | 3/1989 | Kitamura et al. | |
| 4,820,015 | 4/1989 | Mogi | 385/115 |
| 4,914,284 | 4/1990 | Halldorsson et al. | 250/227.29 |
| 4,919,891 | 4/1990 | Yafuso et al. | 356/39 |
| 4,948,256 | 8/1990 | Lin et al. | 356/446 |
| 5,030,000 | 7/1991 | Kanda | 356/40 |
| 5,166,756 | 11/1992 | McGee et al. | 356/446 |
| 5,278,412 | 1/1994 | DeThomas et al. | 250/343 |
| 5,351,322 | 9/1994 | VonBargen | 385/31 |
| 5,402,508 | 3/1995 | O'Rourke et al. | 385/12 |

FOREIGN PATENT DOCUMENTS 2-276947  11/1990  Japan ................ 250/227.29

*Primary Examiner*—Frank Gonzalez
*Assistant Examiner*—Jason D. Eisenberg
*Attorney, Agent, or Firm*—Watson Cole Stevens Davis, P.L.L.C.

[57] ABSTRACT

A diffuse reflectance probe is disclosed which employs in an exemplary embodiment, fiberoptic light transmitting elements and a light pipe for collecting light. The fiberoptic light transmitting elements surround the light pipe and a window having a beveled surface communicates with the light transmitting fiberoptics to direct illuminating radiation in a relatively large field of view in a close working distance with the probe.

29 Claims, 3 Drawing Sheets

DIFFUSE REFLECTANCE PROBE

BACKGROUND OF THE INVENTION

The invention relates to fiberoptic probes. In particular, the invention relates to a fiberoptic probe having a window element of selected thickness and having a beveled surface for directing light towards the sample. The window thickness and angle of the bevel surface are selected so as to result in efficient illumination of the sample at a close working distance; minimizing the reflection that occurs; the high rejection of any specular reflection that occurs; and efficient packaging within the diameter of the probe.

Spectral analysis, and particularly infrared spectroscopy is a known technique which is used to examine samples and monitor online processes. Typically, for an opaque sample, light of a known spectrum is directed at the sample which absorbs and scatters some of the light at various wavelengths. The diffusely reflected portion of the light is collected and analyzed to produce an absorption spectrum which characterizes the sample.

Fiberoptic probes are used to direct light at the sample and to collect the reflected light. The accuracy and sensitivity of the analysis is dependent upon the quality and quantity of the diffusely reflected light collected from the sample. Good collection efficiency results in higher sensitivity. Also, good rejection of any light which has not interacted with the sample, which can degrade measurement sensitivity (noise sources) is desirable.

The intensity of the diffusely reflected light may be improved by increasing the amount of light to the sample. However, it is not always possible to simply increase the light intensity and thereby improve the collection efficiency. Oftentimes, it is more important to accurately position the source light in the field of view of the fiberoptic probe. At the same time, it is important to limit noise sources which can interfere with the reflected light. Such noise sources occur when spurious light which has not interacted with the sample enters the probe. One example of noise is specular reflectance in which some of the source light is reflected into the field of view of the probe. Specular reflectance oftentimes overpowers the return diffuse reflectance signal and thus limits calibration linearity and measurement sensitivity.

Some known probes which are effective to illuminate the sample and collect reflected light with reasonable efficiency are limited in size and do not adapt well to the addition of a window at the distal end of the device. As scale-up of the probe is attempted, collection efficiency decreases and specular reflectance increases. Probes in which the diameter of the collecting fiber is significantly increased to greater than the diameter of the light transmitting fiber tend to have a reduced collection efficiency because light from the illuminating fiber does not effectively illuminate the field of view of the collecting fiber. There tends to be a blind spot in the center of the collecting fiber.

The working distance, is the distance between the probe end and the sample. Collection efficiency is adversely affected as the working distance increases. This is particularly difficult to alleviate with samples which have low reflectance, such as powders, fabrics and the like. Also, powders which have a grain size smaller than the diameter of the fiber oftentimes produce unwanted artifacts which leads to errors in sensor calibration and in measurement accuracy.

Specular reflectance occurs when the illuminating light encounters a surface where the index of refraction changes, for example, at the fiber end face or at a window at the operating end of the probe. The reflected intensity is a function of the angle at which the light encounters the surface. The loss is somewhat dependent upon the angle at which the light encounters the surface. When light reaches the critical angle, incident light is totally internally reflected within the medium. Not only does the occurrence of specular reflectance reduce the total amount of illuminating light available for the sample, the specularly reflected light may enter the collection fiber and thereby reduce or interfere with the sensitivity of the measurement.

It is thus desirable to position the sample illuminating light as close as possible to the probe so that the illuminating light follows a most efficient path. Further, it is desirable to increase the illumination and the spot size of the illuminating light and to locate the same most efficiently within the field of view of the collecting fiber. It is also desirable to not only reduce specular reflectance, but to do so in a way that results in high rejection of any specular reflectance which may occur.

SUMMARY OF THE INVENTION

The present invention is based upon the discovery that a diffuse reflectance probe may provide effective illumination of a sample viewing area at a relatively close working distance by means of a window element that has a beveled surface disposed at the operating end of the probe. The window is effective to direct the illuminating light towards the viewing area at the center of the probe in order to minimize the distance between the illuminated spot and the collection fiber (light collection element) to maximize the collection of the diffusely scattered light. The window is further designed to direct any specularly reflected light off the front face of the window away from the field of view of the collection fiber.

In a particular embodiment, the invention comprises a fiberoptic probe employing a transmitting fiber and a collecting fiber, each having an optical axis and an end-face. The collecting fiber has a field of view. A window element having first, second and third light coupling surfaces including a beveled face surrounding a flat face and a sample viewing face spaced apart therefrom. The beveled surface is located adjacent the end-face of the transmitting fiber and the flat face is located adjacent the collecting fiber. The beveled surface is disposed at a selected angle relative to the axis of the transmitting fiber and the window has a selected thickness. The angle and the thickness are selected so that light is directed towards the field of view of the collecting fiber and achieves maximum illumination at a relatively close working distance to the sample viewing face. Specular reflectance is minimized, and the majority of such specular reflectance is directed beyond the field of view of the collecting fiber.

In another embodiment, the invention comprises a probe having a field of view and including plurality of transmitting fibers surrounding at least one collecting fiber, the transmitting and collecting fibers each have an optical axis in parallel axial alignment and each have a corresponding end-face. A sampling window is located adjacent the end-faces of the transmitting end collecting fibers. The window has a bevel surface lying at an angle with respect to the optical axes of the illuminating fibers. A central surface portion of the window is parallel to the end-faces of the collecting fibers. The window has a sample viewing surface parallel to the central surface portion and spaced away therefrom by a selected distance. The bevel surface transmits illuminating light from the illuminating fibers to a region immediately adjacent the sample viewing surface exterior of the window producing maximum illumination immediately adjacent thereto across the field of view of the probe. The angle and the thickness are chosen so that the illuminating light strikes the sample viewing window at an angle near but less than the critical angle so that the illuminating light illuminates the field of view immediately adjacent the sample viewing window and further such that any light reflected from the sample viewing window is directed away from the field of view of the probe.

In yet another embodiment of the invention, the window is adapted to contact the sample so that the illumination of the sample occurs between the sample contact surface and about a millimeter therefrom.

In yet another embodiment of the invention, the bevel has a conical profile in order to collimate the illuminating radiation towards the sample viewing surface.

In yet another embodiment, the thickness of the window is reduced to allow the probe to be employed for viewing a sample in a transparent vessel.

BRIEF DESCRIPTION OF THE DRAWINGS

FIG. 7 is an alternative embodiment in which a fiberoptic is employed as the light collecting element; and FIG. 8 is an alternative embodiment in which a rigid fiberoptic in the form of a glass rod with an air or glass cladding is employed at the light collecting element.

DESCRIPTION OF THE INVENTION

Figure 1:
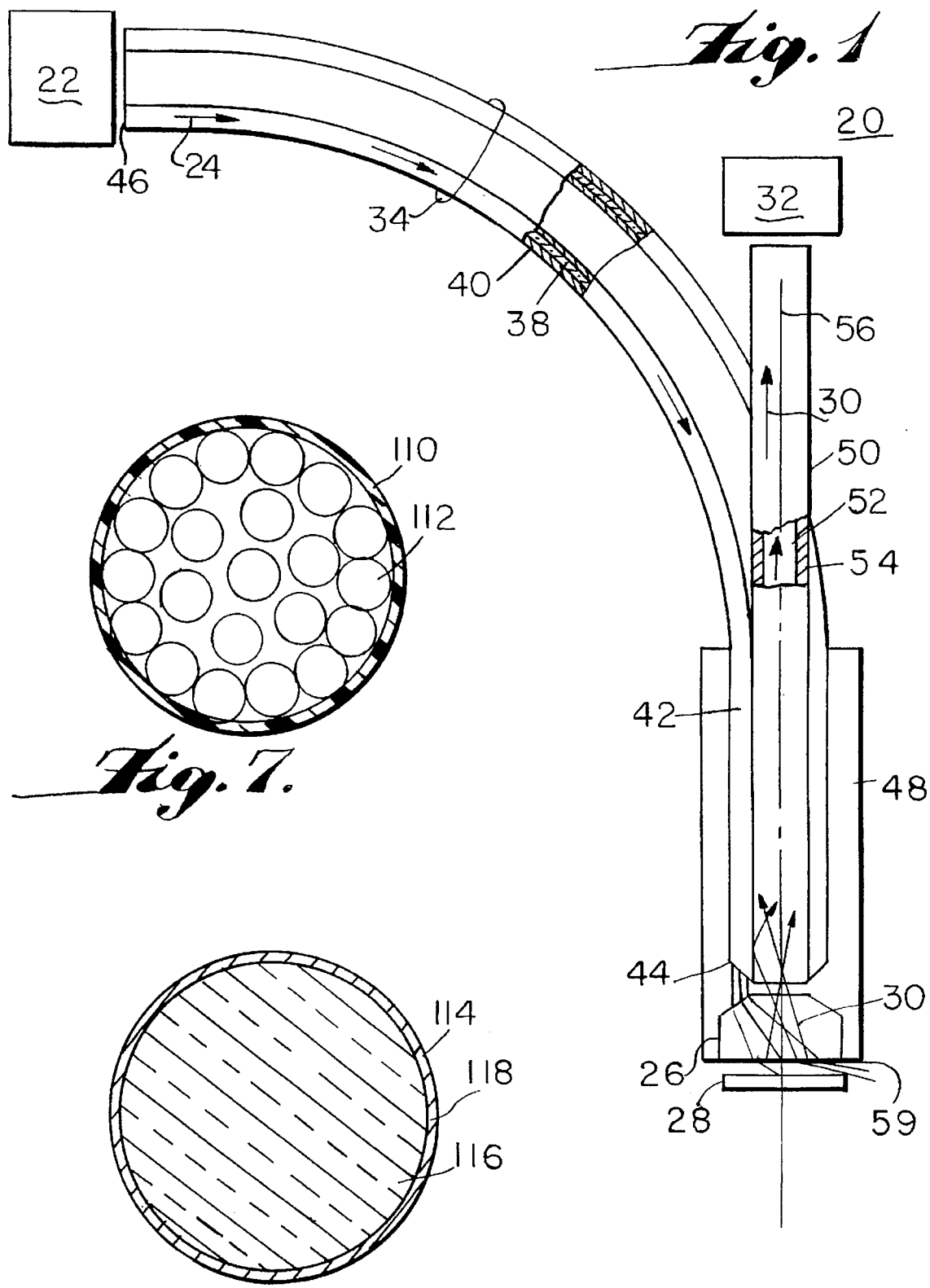
FIG. 1 is a schematic representation of a detector system employing a fiberoptic probe according to the present invention.

FIG. 1 generally illustrates a diffuse reflectance fiberoptic probe 20 according to present invention. The probe 20 is generally used in association with a source 22 of illuminating light 24 which is coupled to the probe 20 and is directed through a sample viewing window 26 at a sample 28. Diffuse reflected light 30 from the sample 28 is carried by the probe to a detector 32 which produces an output for spectrographic analysis. The source of the illuminating light may be provided by a FTIR spectrometer, an acousto-optical tunable filter, a filter potentiometer, a dispersive spectrometer or any other suitable ultraviolet, visible or infrared spectrometer device.

Figure 3:
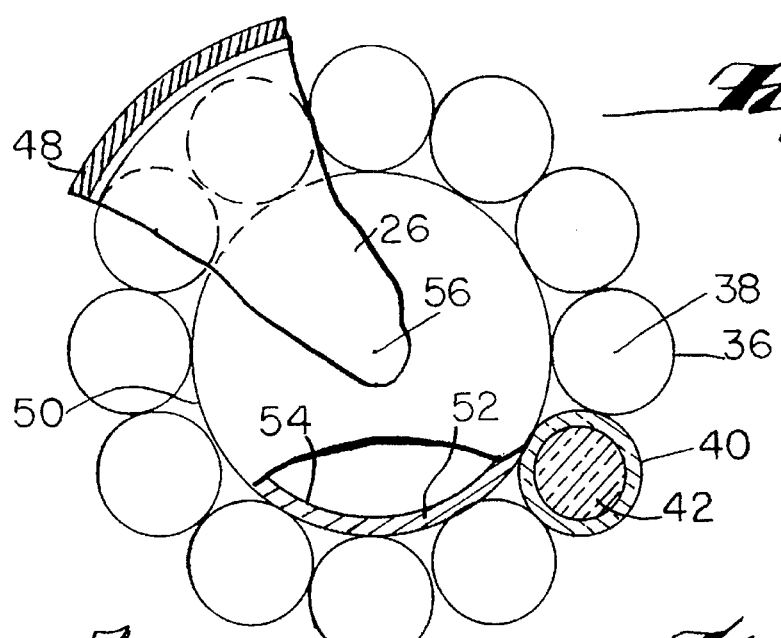
FIG. 3 is a cross-section of the probe taken along line 3—3 of FIG. 2.

In the embodiment illustrated, the probe 20 includes a bundle 34 of illuminating optical fibers 36 formed with a core 38 and cladding 40. Each fiber 34 has a central axis 42, a corresponding end-face 44 and an input end 46 coupled to the source 22 for receiving the illuminating light 24. The bundle 34 of illuminating fibers 36 is arranged in a probe housing 48 in a circular pattern, as illustrated in FIG. 3. A light pipe 50 may be located in the housing 48 concentrically within the circular arrangement of illuminating fibers 40.

The light pipe 50 may be a hollow pipe 52 formed with a reflective gold coating 54 on the interior surface and having a central axis 56 and a corresponding distal end 58. The axes 42 of the fibers 36 and the axis 56 light pipe 50 are arranged within the housing 48 in parallel axial alignment.

It should be understood that the fiber bundle 34 is flexible and extends from the housing 48 to the source 22, as illustrated. The fibers may be formed of a high purity optical glass, or hollow waveguide, or suitable organic materials to form a fiberoptic. An exemplary fiber is formed with a silica core and cladding of lower refractive index so that the numerical aperture (NA) of the fiberoptic is about 0.22. A fluoride fiberoptic may also be employed having a numeric aperture of about 0.2–0.4. The core diameter 38 may be up to about 600 micrometers and the overall diameter may be 630 micrometers for a silica fiber. Fluoride fibers may be smaller with a 250 micrometer core and a 330 micrometer overall diameter. In the embodiment illustrated, the light pipe 50 is rigid and extends from the housing 48 to the detector 32, and has an OD of about 5 mm and ID of about 4 mm and a length of about 100–200 mm. The relatively large ID of the pipe 50 results in a corresponding relatively large viewing. Thus, in the present invention, the ratio of the size of the light transmitting element to the light collecting element is about 3 orders of magnitude. The light pipe 50 may be in the form of a bundle of flexible optical fibers (FIG. 7) or a rigid fiberoptic (FIG. 8), should that be desired.

The window 26 is located within the distal end 59 of the housing 38. The window 26 has light coupling surface 60 and a sample viewing surface 62 which may directly contact the sample 30. The light coupling surface 60 is interior of the housing 48 and includes a beveled surface 64 proximate the end-faces 44 of the fibers 36. The beveled surface 64 resembles an annular conic section and is aligned with the axes 42 of the fibers 36. The light coupling surface 60 also includes a central surface portion 66 which is surrounded by the beveled surface 64 and is parallel to the end face 58 of the light pipe 40. The beveled surface 64 lies at an angle Φ with respect to the horizontal, as shown. The window 26 has an overall thickness dimension T. The dimension T and the angle Φ are chosen so as to provide for minimal specular reflectance without the use of coatings, and to provide a minimal working distance WD between the sample viewing surface 62 and the sample 28. In one embodiment, for example, the window 26 is adapted to be in contact with the sample 28. The end-face 44 of each fiber 36 may be disposed at an angle θ relative to the axis 42 and directed away from the central axis 56, as shown. The end-face may, if desired, be parallel to sample viewing surface 62. The fiber end-faces 44 may be disposed at an outwardly facing angle θ with respect to the horizontal. θ may vary in a range of about 0° and about 35°. The range 15°–25° has been useful for adjusting the working distance and the field of view. The end faces of the fibers may be polished flat, as shown and when arranged as illustrated, to form a polygonal conical surface.

Figure 2:
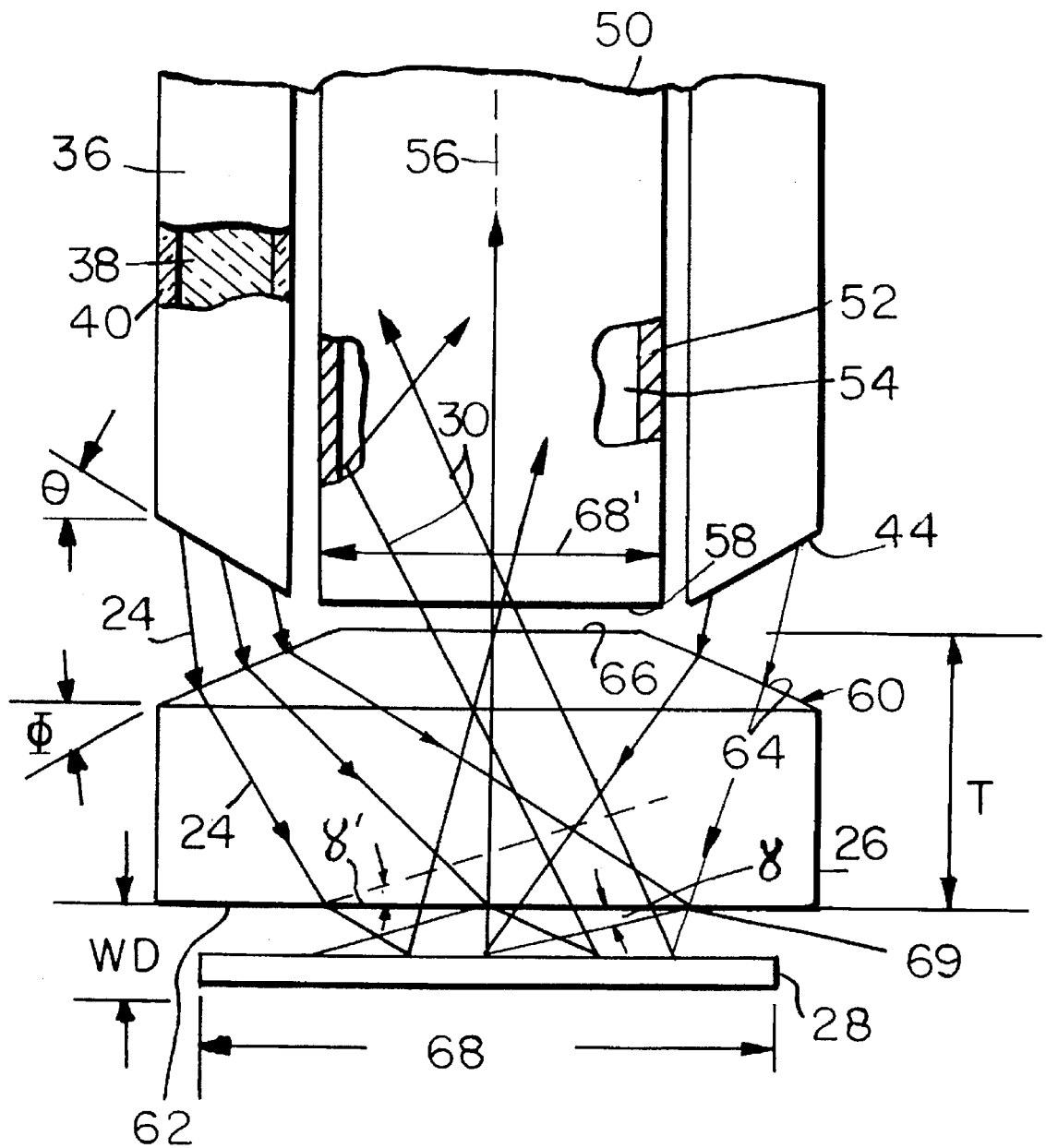
FIG. 2 is a fragmentary cross-section of a sample contacting end of the probe according to the present invention.

As shown in FIG. 2, illuminating light 24, in form of rays, is carried by the illuminating fibers 36 to the end face 44, as shown. The illuminating rays 24 propagate from the end face 44 and impinge on the beveled surface 64, as shown. The light is thereafter carried through the sample window 62 whereupon it illuminates the sample 28. Light scattered from the sample in the form of diffuse reflected rays 30 is carried through the window 26 to the coupling surface 66 and then to the light pipe 50, as illustrated.

Each time a ray encounters a surface which represents a change in refractive index, the light is refracted. In the arrangement illustrated in FIG. 2, the light 24 from the illuminating fiber 36 is refracted towards the central axis 56 as it leaves the end face 44. As the light enters the window 26 at the beveled surface 64, fit is further refracted towards the central axis 56. The illuminating rays 24 exit the sample viewing surface 62 at a shallow angle γ and define a viewing area 68 about the same as the area 68' of the end-face 66 of light pipe 50. As can be seen in FIG. 2, the illuminating light 24 leaving the surface 62 follows a path which is close to the sample viewing surface. Thus, the sample 28 may be illuminated close to the surface 62 within a working distance WD less than about 5 mm. This feature thereby allows the probe 20 to more efficiently illuminate the sample 28 without deep penetration of the light rays. WD may be further reduced to 1 mm or less to allow the probe to contact the sample.

Illuminating light which may be scattered at the viewing surface 62, referred to herein as specularly reflected light, is illustrated by the dotted rays 24'. Specularly reflected light propagates at a shallow angle γ' similar to the angle of the illuminating light. Thus, a majority of the specularly reflected light 24' is carried beyond the field of view 68' of the light pipe 50. In accordance to the invention, therefore, the illuminating radiation is carried to the sample in an area close to the sample viewing surface 62. At the same time, reflected or scattered light from the contact surface is effectively rejected by the systems but it does not enter the light pipe and thereby diminish the sensitivity of the system.

The specular reflectance is minimized in the present invention by careful selection of the bevel angle Φ, the thickness T and the refractive index of the window 28. Also, the specular reflectance may be further reduced by means of an optional anti-reflective coating 69 on the sample viewing surface 62. The specular reflectance resulting in the present invention is less than about 10% of the diffusely reflected light and preferably is less than 5% of said light. The spectral reflectance may be further reduced to less than 1% of the diffusely reflected light by means of the optional anti-reflective coating, the choice of which should be made in accordance with the environment in which the probe is to be used and the desired optical characteristic. The specular reflectance may be measured against a standard diffuse sample sold under the trademark Speculon by LabSphere.

Figure 4:
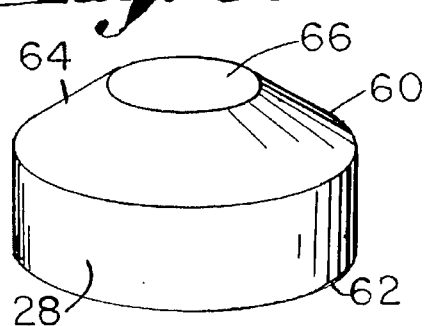
FIG. 4 is a perspective view of a sample window in accordance with an embodiment of the present invention.

As can be seen in FIG. 4, the viewing window 28 comprises a cylindrical member formed with the beveled surface 64 and the flat surface 66 in spaced relation with the sample viewing surface 62 In the arrangement, the bevel surface 64 is in the form of a frustral conical surface. In the arrangement, the illuminating rays 24 tend to diverge across the field of view 68. The advantage of the arrangement of FIG. 4 is relative ease of manufacture.

In the exemplary embodiment illustrated, the window 28 is a sapphire material, having an index or a fraction of about 1.77. The angle Φ is about 45° and the thickness T is about 5 mm. The radius R is about 10 mm. Sapphire is a useful material because it tends to be more chemically robust than other materials.

The angle Φ may vary in a range of about 25° and 65° with the thickness and radius bearing accordingly. Also, as the index of refraction is varied, Φ, T and R may be adjusted. For example, the window 26 may be a BK7 glass having an index of refraction of 1.5. Thus, the values of θ, T and R may be varied to the thereby maximize the viewing area and minimize specular reflection.

Figure 5:
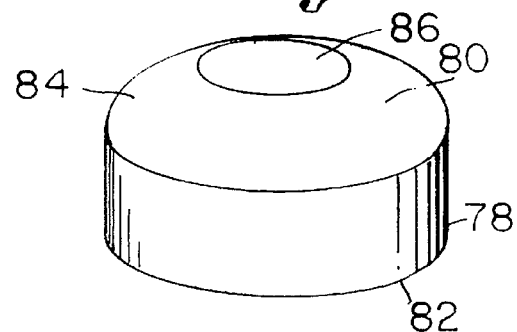
FIG. 5 is a perspective view of a sample window according to an alternative embodiment of the invention.

FIG. 5 illustrates an alternative embodiment of a sample viewing window having light coupling surface 80 and a sample viewing surface 82. The light coupling surface 80 includes an outer chamfered portion 84 and surrounding a central flat portion 86. The sample viewing surface 82 is similar to the arrangement of FIG. 4. The chamfered light coupling surface 84 acts like a lens and tends to collimate the illuminating radiation.

Figure 6:
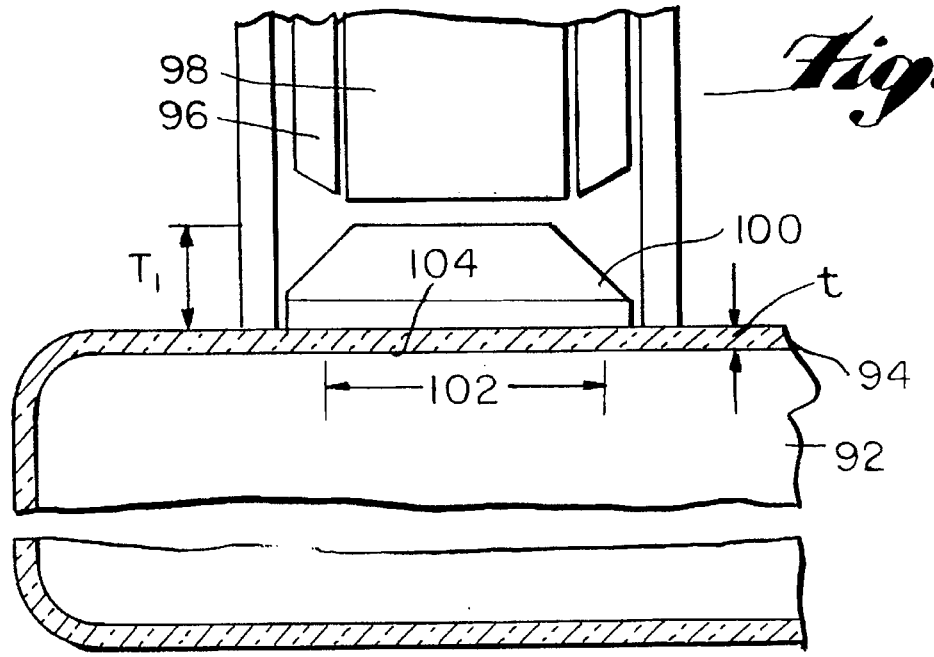
FIG. 6 is a fragmentary side elevation of another embodiment of the invention for sensing a sample located in a transparent vial.

FIG. 6 is a fragmentary illustration of an alternative embodiment of the invention in the form of a probe 90 adapted for viewing a sample 92 in a vial 94 having a wall thickness t. In the arrangement illustrated in FIG. 1, if the probe 20 is placed in direct contact with the vial 94 or other glass window, for example, the illumination radiation tends to diverge appreciably before it reaches the sample 92. This can lead to a loss of inefficiency in the level of reflected radiation measured from the sample versus the measurement of the same sample in direct contact with the probe window.

The arrangement in FIG. 6 is similar to that of FIG. 1 and employs a plurality of flexible fiberoptics 96 surrounding a light pipe 98 and a viewing window 100 which is similar to the window 28. However, in the arrangement of FIG. 6, the window 100 has a thickness T' which is less than the thickness T of the window 28. Further, the thickness T' is reduced by approximately the thickness t of the vial wall 94. Thus, the illumination becomes less diffuse and tends to be more concentrated in the field of view 102 immediately adjacent the inside surface 104 of the vial 94. In general, the refractive index of the vial 94 is less than the refractive index of the window 100 and an adjustment may be made in the choice of the window materials and thickness T'.

In accordance with the present invention, the working distance WD of the probes illustrated herein may be variously adjusted by adjusting the angle Φ of the bevel surface 64. When the working distance WD is advantageously reduced, the return signal 30 is normally improved and the scattered reflection is reduced. The angle Φ may be dependent on the refractive index of the window.

Likewise, the angle θ of the fiber 36 may be varied as noted to tailor the path of the illuminating radiation 24. The window thickness T may be in a range of about 5 and about 10 mm, for a sapphire material. In the arrangement of FIG. 6, T' may be reduced by the vial thickness t, although overall, the sum of T'+t may be in the range noted above.

FIG. 7 illustrates an alternative embodiment in which a flexible fiberoptic 110 formed of a plurality of individual fiberoptics 112 may be substituted for the light pipe 50. Likewise, a single fiberoptic 114, illustrated in FIG. 8, may be employed as the light collecting element which comprises a glass core 116 having a cladding 118.

It should be understood that the sample 28 illustrated in the various embodiments is a schematic illustration of a substance which may be in the form of a powder, a liquid or a textile material as well as any other material, whether reflective or not for which a desirable reflectance measurement might be required.

While there have been described what are at present considered to be the preferred embodiments of the present invention, it will be apparent to those skilled in the art that various changes and modifications may be made therein without departing from the invention, and it is intended in the appended claims to cover such changes and modifications as fall within the spirit and scope of the invention.

What is claimed is:

1. A probe for viewing a sample in a viewing area immediately adjacent the probe comprising:

a light transmitting element having a first axis and a first distal end for transmitting light;

a light collecting element having a second axis and a second distal end being located adjacent to the light transmitting element for collecting light; and a sample viewing window disposed adjacent the first and second distal ends, said sample viewing window having sample viewing surface and a light coupling surface including a peripheral bevel surface in communication with the light transmitting element proximate the first distal end and central end face in communication with the light collecting element proximate the second distal end, said light transmitting element and said light collecting element being in optical communication with the viewing area through said window so that when a sample is positioned within the viewing area proximate the sample viewing surface a substantial portion of the light transmitted by light transmitting element is directed from the first distal end to the bevel surface through the window into the viewing area and is reflected by the sample through the window as diffusely reflected light and is collected from the end face by the second distal end of the light collecting element, said bevel surface of the window resulting in a working distance of the viewing area within about 5 mm of said window.

2. The probe of claim 1 wherein the bevel surface comprises a frustro conical surface.

3. The probe of claim 1 wherein the bevel surface lies at an angle in a range of about 25° to about 65°.

4. The probe of claim 1 wherein the bevel surface lies at an angle of about 45° with respect to the horizontal.

5. The probe of claim 1 wherein the light transmitting element comprises first and second fiberoptics.

6. The probe of claim 5 further including a housing for securing the first and second fiberoptics in parallel axial alignment.

7. The probe of claim 1 wherein the first light transmitting element comprises a fiberoptic having an end-face proximate the window at the distal end.

8. The probe of claim 7 wherein the end-face of the fiberoptic lies at an angle with respect to the central axis thereof.

9. The probe of claim 8 wherein the angle is in a range of about 0° to about 35°.

10. The probe of claim 8 wherein the angle is in a range of about 15° to about 25°.

11. The probe of claim 1 wherein the bevel angle results in minimized specular reflectance.

12. The probe of claim 1 wherein the window geometry results in a specular reflectance of less than about 10% of the diffusely reflected light.

13. The probe of claim 12 wherein the specular reflectance is less than about 5% of the diffusely reflected light.

14. The probe of claim 12 wherein the specular reflectance less than about 1% of the diffusely reflected light.

15. The probe of claim 12 wherein the diffusely reflected light is produced by a standard sample.

16. The probe of claim 12 wherein the bevel angle results in maximized rejection of specular reflectance from the sample viewing window.

17. The probe of claim 1 further including an anti-reflective coating on the sample viewing surface for reducing specular reflectance.

18. The probe of claim 1 wherein the light coupling surface comprises a chamfer for collimating illuminating radiation through the window.

19. The probe of claim 1 wherein the window has a thickness T sufficient to result in transmission of illuminating light across a field of view including the central axis of the light collecting element.

20. The probe of claim 1 wherein the window is located proximate to distal end of the probe for contacting the sample.

21. The probe of claim 1 wherein the working distance is in a range of about 0 to about 1 mm.

22. The probe of claim 1 wherein the probe is operative for contact with the sample.

23. The probe of claim 1 wherein the light collecting element comprises at least one of a light pipe of flexible fiberoptic and a rigid fiberoptic.

24. The probe of claim 1 wherein the light collecting element and the light transmitting element are in a size ratio of about 3 orders of magnitude.

25. The probe of claim 1 wherein the window has a thickness of a size compatible with viewing a sample through a transparent container.

26. The probe of claim 1 further comprising a light source including at least one of a FTIR spectrometer, an acousto-optical tuneable filter, a filter photometer, a dispersive spectrometer and a spectrometer for providing at least one of ultraviolet, visible and infrared light.

27. The probe of claim 1 wherein the window includes one of a bevel angle of the bevel surface and a thickness of the window.

28. The probe of claim 1 wherein the bevel surface is intermediate the first distal end and the sample viewing window.

29. A diffuse reflectance probe for viewing a sample in a viewing area immediately adjacent the probe comprising:

a light transmitting waveguide having a first axis and a distal end for transmitting light to the distal end;

a light collecting waveguide having a second axis and a second distal end being located adjacent to the first distal end of light transmitting waveguide for collecting light at the second distal end; and a sample viewing window for contacting the sample disposed adjacent the distal ends of the waveguides, said sample viewing window having a light coupling surface including a bevel surface in communication with the light transmitting waveguide, the respective first and second distal ends of said light transmitting waveguide and said light collecting waveguide being in optical communication with the viewing area through said window so that when a sample is positioned within the viewing area, light transmitted by light transmitting waveguide is directed through the window into the viewing area and is diffusely reflected with minimal specular reflectance by the sample through the window and is collected by the light collecting waveguide.

* * * * *